United States Patent [19]

Spietschka et al.

[11] Patent Number: 4,709,029
[45] Date of Patent: * Nov. 24, 1987

[54] PROCESS FOR THE PREPARATION OF PERYLENE-3,4,9,10-TETRACARBOXYLIC ACID MONOANHYDRIDE MONOIMIDES

[75] Inventors: Ernst Spietschka, Idstein; Helmut Tröster, Königstein, both of Fed. Rep. of Germany

[73] Assignee: Hoechst Aktiengesellschaft, Frankfurt am Main, Fed. Rep. of Germany

[*] Notice: The portion of the term of this patent subsequent to Jul. 8, 2003 has been disclaimed.

[21] Appl. No.: 821,618

[22] Filed: Jan. 23, 1986

Related U.S. Application Data

[60] Division of Ser. No. 599,202, Apr. 11, 1984, Pat. No. 4,599,408, which is a continuation of Ser. No. 261,454, May 7, 1981, abandoned.

Foreign Application Priority Data

May 5, 1980 [DE] Fed. Rep. of Germany ....... 3017185

[51] Int. Cl.$^4$ .................. C07D 491/06; C07D 413/06
[52] U.S. Cl. ........................................ 544/125; 546/37
[58] Field of Search ............................ 546/37, 38, 39; 544/125

[56] References Cited

U.S. PATENT DOCUMENTS

| | | | |
|---|---|---|---|
| 2,543,747 | 3/1951 | Schrader | 546/37 |
| 4,141,881 | 2/1979 | Babler | 546/37 |
| 4,153,602 | 5/1979 | Schiessler et al. | 546/37 |

Primary Examiner—Alan L. Rotman
Attorney, Agent, or Firm—Curtis, Morris & Safford

[57] ABSTRACT

Compounds of the formula

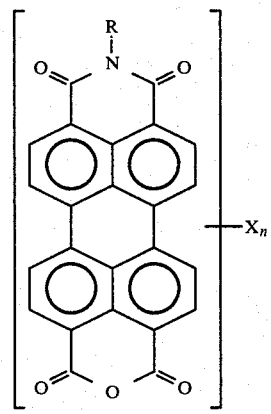

in which R denotes hydrogen, hydroxyl, amino or optionally substituted alkyl, X denotes chlorine or bromine and n is a number from zero to 4, are obtained from the corresponding mono-alkali metal salts of perylene-3,4,9,10-tetracarboxylic acid monoanhydrides by reaction with compounds of the formula R-NH$_2$, in which R has the above meaning, at 0°-130° C. The compounds are colorants or starting materials for colorants.

6 Claims, No Drawings

PROCESS FOR THE PREPARATION OF PERYLENE-3,4,9,10-TETRACARBOXYLIC ACID MONOANHYDRIDE MONOIMIDES

This application is a division of application Ser. No. 599,202, filed Apr. 11, 1984 now U.S. Pat. No. 4,599,408 which is a continuation of application Ser. No. 261,454 filed May 7, 1981, now abandoned.

The invention relates to perylene-3,4,9,10-tetracarboxylic acid monoanhydride monoimides of the formula 1

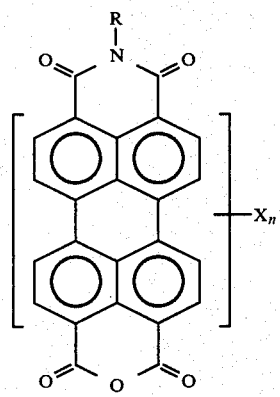

in which R denotes hydrogen, hydroxy, amino, cycloalkyl with 4 to 8 C atoms or alkyl which has 1 to 8 C atoms, unsubstituted or substituted by cycloalkyl with 4 to 8 C atoms, phenyl, or phenyl substituted by halogen, lower alkyl, lower alkoxy or lower alkoxycarbonyl, or R is alkyl of 1 to 8 C atoms, substituted by cyano, hydroxy, carbamoyl, acyl, lower dialkylamino, morpholyl, piperidyl or alkoxy which has 1 to 8 C atoms, unsubstituted or substituted by hydroxy, lower alkoxy, lower hydroxyalkyl, cyano, cycloalkyl with 4 to 8 C atoms or phenyl, X denotes chlorine or bromine and n denotes a number from 0 to 4, and in which R does not denote the group

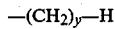

$-(CH_2)_y-H$ in which y is a number from 0 to 4, if n is zero.

Those compounds in which n denotes 0 are particularly preferred.

The invention also relates to a process for the preparation of perylene-3,4,9,10-tetracarboxylic acid monoanhydride monoimides of the formula 1, in which R represents hydrogen, amino, hydroxy, or an optionally substituted alkyl group, X denotes chlorine or bromine and n denotes a number from 0 to 4.

The preparation of perylene-3,4,9,10-tetracarboxylic acid monoanhydride monoimide by partial saponification of the corresponding diimide with sulfuric acid is known (German Patent Specification No. 411,217). However, the process gives a yield of only 55% (Nagao et al., Kogyo Kagaku Zasshi 1971, 74 (12), pages 2,500 to 2,502).

The reaction of perylene-3,4,9,10-tetracarboxylic acid dianhydride with alkylamines, which leads to the diimides via the monoimides, is investigated in Nippon Kagaku Kaishi, 1979 (4), pages 528–34. The monoimides intermediately formed are determined in the reaction mixture by spectrophotometry, maximum yields of 62–84% being given (paragraphs 2.3 and 2.4, page 529, and Table 3, page 530). The yields actually achieved for the monoimides isolated from the reaction mixture were, however, only 24–46% (paragraph 2.2 and Table 1, page 529). Besides the unsatisfactory yields, this procedure has the disadvantage that it requires continuous analytical examination of the course of the reaction.

It has now been found that perylene-3,4,9,10-tetracarboxylic acid monoanhydride monoimides of the formula 1 can be obtained by a process which comprises reacting mono-alkali metal salts of perylene-3,4,9,10-tetracarboxylic acid monoanhydrides, of the formula 2

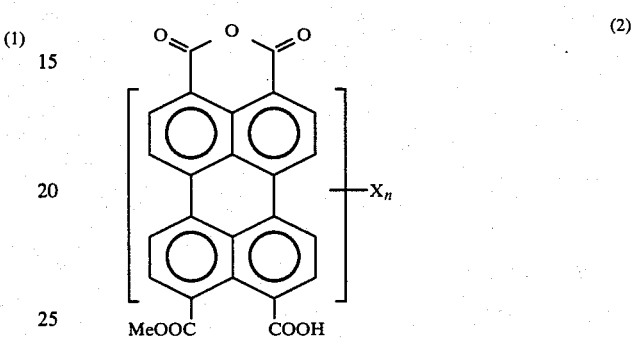

in which Me represents a sodium or potassium atom and X and n have the abovementioned meaning, with compounds of the formula 3

$R-NH_2$ (3)

wherein R denotes hydrogen, amino, hydroxy or an optionally substituted alkyl group, at 0°–130° C., preferably at 0°–95° C.

The new process gives the corresponding perylene-3,4,9,10-tetracarboxylic acid monoanhydride monoimides in high, in some cases almost quantitative, yields in a simple manner, without special monitoring of the course of the reaction being necessary.

Preferred embodiments of the invention are described in more detail below:

The starting compounds of the formula 2 can be prepared by the process described in U.S. patent application Ser. No. 239,909, filed Mar. 3, 1981. In this process, three equivalents of acid, such as hydrochloric acid, sulfuric acid, nitric acid or phosphoric acid, are added to an aqueous solution or suspension of a tetra-alkali metal salt or tetraammonium salt of the corresponding perylene-3,4,9,10-tetracarboxylic acid at about 20°–100° C., preferably 70°–95° C. If an ammonium salt is employed, at least one equivalent of sodium or potassium ions must be present. Intermediate isolation of these compounds is not necessary. It is thus possible for them to be reacted with the compounds of the formula 3 in the form in which they are obtained in the reaction mixture during synthesis.

Particularly preferred starting substances of the formula 2 are those in which n denotes O and Me denotes potassium.

Examples of starting substances of the formula 3 are ammonia, hydrazine, hydroxylamine, methyl-, ethyl-, propyl-, butyl- and octyl-amine, benzylamine, ethanol-, isopropanol- and hydroxypropyl-amine, methoxypropyl-, butoxypropyl-, butoxyethoxypropyl-, octyloxypropyl-, 2-ethylhexyloxypropyl- and 3-morpholinopropyl-amine, cyclohexylamine, 2-cyanoethylamine, 2- chloro- or -bromo-ethylamine, carbamoylethylamine and cyclohexyloxypropyl- and benzyloxypropyl-amine.

At least 2 moles, preferably 3 moles or even a larger excess, of the compound 3 are employed per mole of starting substance of the formula 2. The condensation is carried out in water at temperatures from 0° to 130° C., preferably at 0°–95° C. It is expedient to follow a procedure which comprises introducing the mono-alkali metal salt of the monoanhydride into an amine/water mixture, or adding the amine of the formula 3 to an aqueous suspension of the mono-alkali metal salt of the monoanhydride.

The reactants can be combined at 0°–95° C. It is expedient to prepare the reaction mixture at lower temperatures of about 0°–30° C. and then to bring the condensation reaction to completion at higher temperatures of about 70°–95° C. The reaction to give the monoimide has in general ended after 1–2 hours at 90°–95° C.

The reaction product is then obtained from the reaction mixture by acidification, for example with mineral acids, preferably at the higher temperature of about 70°–95° C. It is isolated in the customary manner, for example by filtration. If necessary, the product can also be freed from small amounts of diimide which have also been formed and from perylenetetracarboxylic acid dianhydride, for example in accordance with the statements made in Nippon Kagaku Kaishi loc. cit. paragraph 2.2, page 529, by a procedure in which the alkali-insoluble diimide is removed by alkaline clarifying filtration and the perylenetetracarboxylic acid dianhydride is separated off, via its readily soluble tetrapotassium salt, from the dipotassium salt of the end product, which is frequently sparingly soluble.

Most of the process products obtained are new. They are valuable starting materials for the preparation of colorants. However, they can also themselves be used as colorants, if necessary after appropriate conditioning.

In the following examples, the percentage data relate to the weight, unless indicated otherwise.

EXAMPLE 11

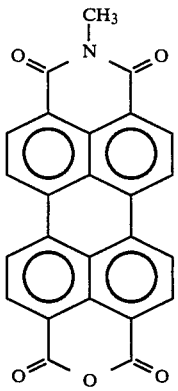

10.3 g of methylamine solution (45.4% strength) are poured into a suspension of 22.4 g of the mono-potassium salt of perylene-3,4,9,10-tetracarboxylic acid monoanhydride in 250 ml of water at 0°–5° C., and the mixture is stirred at 0°–5° C. for 12 hours. 27.0 g of 50% strength potassium hydroxide solution are then added, and the temperature of the mixture is kept at 90° C. for 1 hour. The reaction product is filtered off at 20°–25° C. and, in order to remove traces of the tetra-potassium salt of the perylenetetracarboxylic acid, is washed with 5% strength potassium hydroxide solution until the filtrate runnings are colorless. The residue on the filter is dissolved in 300 ml of water at 90°–95° C., and traces of the perylenetetracarboxylic acid diimide are filtered off hot. Perylene-3,4,9,10-tetracarboxylic acid monoanhydride monomethylimide is precipitated from the filtrate by acidification with concentrated hydrochloric acid, filtered off, washed until free from chloride and dried.

Yield: 19.4 g (95.8% of theory).

| Analysis: | calculated: | C 74.1% | found: | C 73.7% |
|---|---|---|---|---|
| | | H 2.7% | | H 2.8% |
| | | N 3.5% | | N 3.5% |

EXAMPLE 12

124 g of methylamine (45.4% strength) are added at 20°–25° C. to a suspension of the mono-potassium salt of perylenetetracarboxylic acid monoanhydride, which has been obtained from 196 g of perylenetetracarboxylic acid dianhydride (without intermediate isolation of the mono-potassium salt) according to Example 3. The mixture is then warmed to 90°–95° C. After 1 hour, 160 g of 50% strength potassium hydroxide solution are allowed to run in and the mixture is subsequently stirred for a further hour at the same temperature.

The red di-potassium salt, which has crystallized out, of the monomethylimide is filtered off at room temperature, washed with an aqueous solution of 3% of potassium chloride and 1% of potassium hydroxide until the filtrate runnings are colorless, and worked up as indicated in Example 11 to give an identical end product.

Yield: 191.7 g (94.7% of theory, relative to the perylenetetracarboxylic acid dianhydride).

EXAMPLE 13

If the procedure followed is as indicated in Example 11, but the mono-sodium salt (Na content of 3.5%=65.8% of mono-sodium salt) is used instead of the mono-potassium salt, 13.0 g (64.2%) of an identical end product are obtained.

EXAMPLE 14

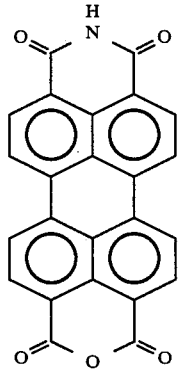

22.4 g of the mono-potassium salt of perylenetetracarboxylic acid monoanhydride are introduced into 280 g of aqueous 3% strength ammonia solution at 0°–5° C., and the mixture is subsequently stirred for 4 hours, without further cooling. The mixture is then warmed to 90°–95° C. and stirred at this temperature for 2 hours.

After the addition of a solution of 15 g of potassium carbonate (anhydrous) in 50 ml of water, the mixture is stirred for a further hour at 90° C. The product is filtered off at 20°-25° C. and, in order to remove a small amount of the tetra-potassium salt of the perylenetetracarboxylic acid, is washed with 2% strength potassium carbonate solution until the filtrate runnings are colorless.

The residue is dissolved in 1,300 g of 3.5% strength potassium hydroxide solution at 95° C., and a trace of perylenetetracarboxylic acid diimide is separated off by filtration. The reaction product is precipitated from the hot filtrate with hydrochloric acid (31% strength) and isolated in the customary manner. 17.9 g (91.6%) of perylenetetracarboxylic acid monoanhydride monoimide are obtained.

Analysis: calculated: N 3.5%, found: N 3.5%.

EXAMPLE 15

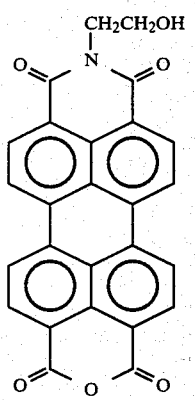

22.4 g of the mono-potassium salt of perylenetetracarboxylic acid monoanhydride are introduced into an aqueous solution of 13.5 g of ethanolamine in 250 ml of water, and the mixture is stirred at 20°-30° C. for 2 hours and at 90°-95° C. for 2 hours. The dark red solution is then clarified hot and the reaction product is precipitated by acidification and isolated in a known manner. To remove a small amount of perylenetetracarboxylic acid, the product is warmed to 90° C. in 200 ml of 5% strength potassium hydroxide solution and the di-potassium salt is salted out by adding 20 g of potassium chloride. The product, which is filtered off at room temperature, is washed with an aqueous solution of 3% of potassium chloride and 1% of potassium hydroxide, the residue is dissolved in 500 ml of water and the product is precipitated under acid conditions and isolated, in the customary manner.

Yield: 20.0 g (91.9%).

| Analysis: | calculated: | C 71.7% | found: | C 71.0% |
|---|---|---|---|---|
| | | H 3.0% | | H 3.0% |
| | | N 3.2% | | N 3.2% |

EXAMPLE 16

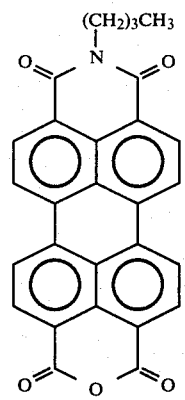

22.4 g of the mono-potassium salt of perylenetetracarboxylic acid monoanhydride are introduced into a solution of 14.6 g of butylamine in 250 ml of water at room temperature, and the mixture is stirred at 20°-25° C. for 5 hours and at 90° C. for 1 hour. The reaction product is then precipitated under acid conditions and isolated. In order to separate off small amounts of diimide and perylenetetracarboxylic acid, the substance is dissolved in 350 ml of 5% strength potassium hydroxide solution at 90°-95° C. and the di-potassium salt is precipitated by adding 30 g of potassium chloride. The salt is filtered off at room temperature and washed with an aqueous solution of 14% of potassium chloride and 1% of potassium hydroxide. The residue is dissolved in water at the boiling point and the solution is clarified from traces of diimide. 19.4 g (86.8%) of perylenetetracarboxylic acid monoanhydride monobutylimide are obtained by acidification of the filtrate and customary isolation.

Analysis: calculated: N 3.1%, found: N 3.1%.

EXAMPLE 17

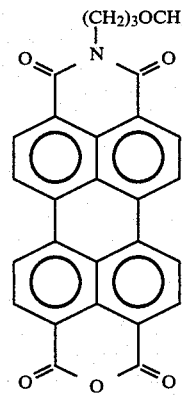

22.4 g of the mono-potassium salt of perylenetetracarboxylic acid monoanhydride are reacted with 19.6 g of 3-methoxypropylamine as described in Example 16. Before the acid precipitation, the mixture is clarified, after dilution with 500 ml of water, from a small amount of diimide. 22.0 g (95.0%) of reaction product are obtained.

Analysis: calculated: N 3.0%, found: N 2.7%.

EXAMPLE 18

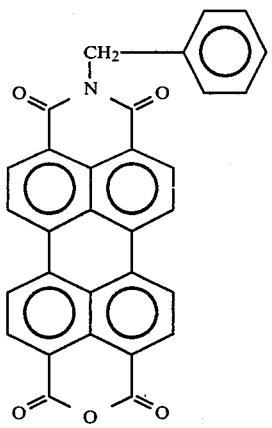

44.8 of the mono-potassium salt of perylenetetracarboxylic acid monoanhydride are introduced into an ice-cold solution of 47 g of benzylamine in 500 ml of water, the mixture is warmed slowly to 90°–95° C. and, after 2 hours, 60 g of 50% strength potassium hydroxide solution are added and the di-potassium salt is salted out with 25 g of potassium chloride. After working up according to Example 17, perylenetetracarboxylic acid monoanhydride monobenzylimide is obtained in a yield of 44.0 g (91.5%).

Analysis: calculated: N 2.9%, found: N 2.6%.

EXAMPLE 19

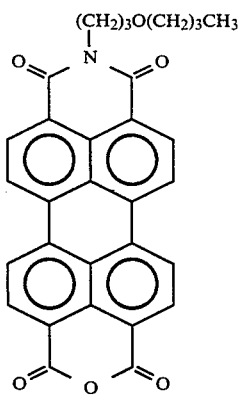

The procedure followed is as according to Example 17, 28.8 g of butoxypropylamine being employed instead of 3-methoxypropylamine. The reaction product is obtained in a yield of 22.6 g (89.5%).

| Analysis: | calculated: | C 73.7% | found: | C 73.3% |
|---|---|---|---|---|
| | | H 4.5% | | H 4.5% |
| | | N 2.8% | | N 2.7% |

EXAMPLE 20

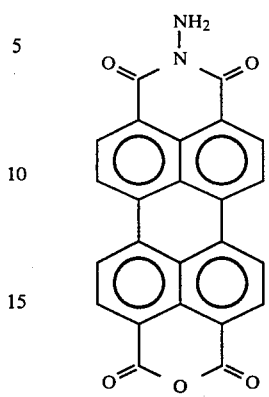

A mixture of 300 ml of water, 13.8 g of hydrazine hydrate (80% strength) and 22.4 g of the mono-potassium salt of perylenetetracarboxylic acid monoanhydride is warmed to 90° C. and is kept at this temperature for 3 hours. It is then diluted with 500 ml of water and clarified hot. The reaction product, which has been precipitated from the filtrate with acid and isolated in the customary manner, is converted into the di-potassium salt by treatment with 400 ml of hot 5% strength potassium hydroxide solution. After customary working up, 18.2 g (89.7%) of perylenetetracarboxylic acid monoanhydride mono-N-aminoimide are obtained.

| Analysis: | calculated: | C 70.9% | found: | C 70.4% |
|---|---|---|---|---|
| | | H 2.5% | | H 2.4% |
| | | N 6.9% | | N 6.9% |

EXAMPLE 21

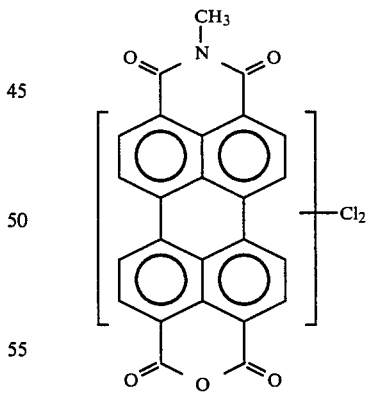

Following the procedure of Example 16, 20.7 g of the mono-potassium salt of dichloroperylenetetracarboxylic acid monoanhydride, prepared from dichloroperylenetetracarboxylic acid dianhydride according to Example 10 in 250 ml of water are reacted with 10.8 g of 45.4% strength methylamine solution to give the corresponding monoanhydride monomethylimide.

Yield: 10.4 g (54.8%). Analysis: calculated: N 3.0%, found: N 3.1%.

EXAMPLE 22

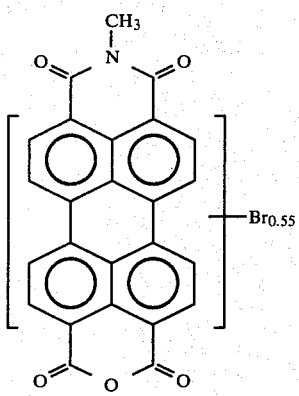

21.1 g of the mono-potassium salt of bromoperylene-tetracarboxylic acid monoanhydride, prepared according to Example 9 are suspended in 250 ml of water, and 9.8 g of methylamine solution (45.4% strength) are added. The mixture is subsequently stirred at 20°–25° C. for 2 hours, and 28 g of 50% strength potassium hydroxide solution are then allowed to run in. The mixture is kept at 90° C. for 1 hour and then cooled to 20° C. and filtered. The reaction product is isolated in a yield of 16.5 g (92%) according to Example 16, from the dipotassium salt thus obtained.

| Analysis: | calculated: | Br 9.8% | found: | Br 10.3% |
|---|---|---|---|---|
| | | N 3.1% | | N 3.3% |

The table which follows contains further perylene-3,4,9,10-tetracarboxylic acid monoanhydride monoimides, which are obtained by procedures corresponding to those described in the above examples:

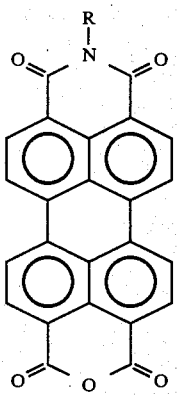

| | | Analysis | |
|---|---|---|---|
| Example | R | calculated | found |
| 23 | —(CH$_2$)$_7$CH$_3$ | 2.8% N | 2.9% N |
| 24 | —(CH$_2$)$_3$OCH$_2$CH((CH$_2$)$_3$CH$_3$)C$_2$H$_5$ | 2.5% N | 2.7% N |
| 25 | —CH$_2$CHCH$_3$ \| OH | 3.1% N | 3.0% N |
| 26 | —(CH$_2$)$_2$N(C$_2$H$_5$)$_2$ | 5.7% N | 5.5% N |
| 27 | —(CH$_2$)$_3$—N(morpholine) | 5.4% N | 5.1% N |
| 28 | —OH | 3.4% N | 3.5% N |
| 29 | —CH$_2$—C$_6$H$_4$—CH$_3$ | 2.8% N | |
| 30 | —CH$_2$—C$_6$H$_4$—Cl | 6.9% Cl | |

We claim:

1. A process for the preparation of perylene-3,4,9,10-tetracarboxylic acid anhydride monoimides of the formula

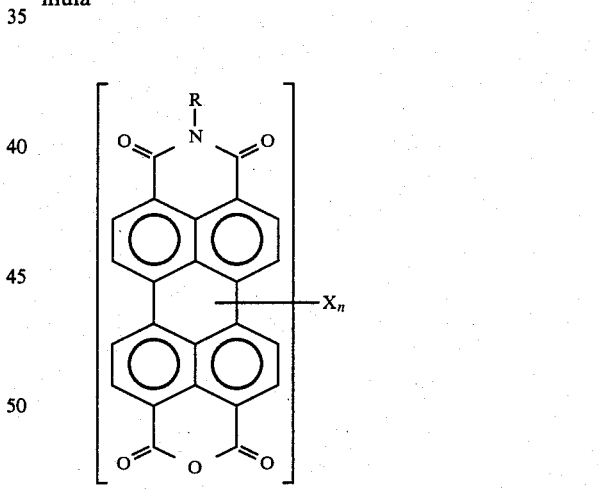

in which R is hydrogen, amino or alkyl of 1 to 4 carbon atoms which is unsubstituted or substituted by cycloalkyl of 4 to 8 carbon atoms, cyano, hydroxy, carbamoyl, lower dialkylamino, morpholyl, phenyl which is unsubstituted or substituted by halogen or lower alkyl, or alkoxy of 1 of 8 carbon atoms which is unsubstituted or substituted by lower alkoxy; X is chlorine or bromine; and n is a number from 0 to 4, which comprises reacting a monoalkali metal salt of perylene-3,4,9,10-tetracarboxylic acid monoanhydride, of the formula

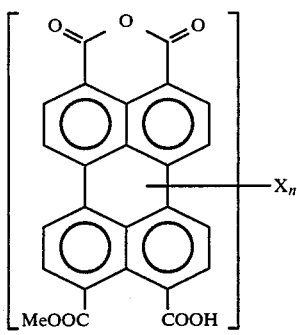

in which Me is sodium or potassium and X and n have the abovementioned meaning, with a compound of the formula R—NH$_2$ in which R has the abovementioned meaning, at 0°–130° C.

2. The process as claimed in claim 1, in which n is a number from 0 to 2.

3. A process as claimed in claim 1, wherein Me is potassium and n is 0.

4. A process as claimed in claim 1, wherein the reaction is carried out at 0°–95° C.

5. The process as claimed in claim 1, wherein the reaction is carried out at 0° to 95° C., and at least two mols of RNH$_2$ are employed per mol of monoalkali metal salt.

6. The process as claimed in claim 1, wherein at least three mols of RNH$_2$ are employed per mol of monoalkali metal salt, and the reaction is carried out in water.

* * * * *